(12) United States Patent
Mileni

(10) Patent No.: US 12,351,628 B2
(45) Date of Patent: *Jul. 8, 2025

(54) MODIFIED MEMBRANE SPANNING PROTEINS AND METHODS FOR THE PREPARATION AND USE THEREOF

(71) Applicant: Abilita Bio, Inc., San Diego, CA (US)

(72) Inventor: Mauro Mileni, San Diego, CA (US)

(73) Assignee: ABILITA THERAPEUTICS, INC., San Diego, CA (US)

( * ) Notice: Subject to any disclaimer, the term of this patent is extended or adjusted under 35 U.S.C. 154(b) by 863 days.

This patent is subject to a terminal disclaimer.

(21) Appl. No.: 17/335,677

(22) Filed: Jun. 1, 2021

(65) Prior Publication Data

US 2021/0363239 A1 Nov. 25, 2021

Related U.S. Application Data

(63) Continuation of application No. 16/411,059, filed on May 13, 2019, now Pat. No. 11,053,312, which is a continuation of application No. 14/928,128, filed on Oct. 30, 2015, now Pat. No. 10,287,349.

(60) Provisional application No. 62/073,554, filed on Oct. 31, 2014.

(51) Int. Cl.
*C07K 16/28* (2006.01)
*C07K 14/705* (2006.01)
*C12N 15/10* (2006.01)
*A61K 38/00* (2006.01)

(52) U.S. Cl.
CPC ............ *C07K 16/28* (2013.01); *C07K 14/705* (2013.01); *C12N 15/1037* (2013.01); *C12N 15/1079* (2013.01); *C12N 15/1093* (2013.01); *A61K 38/00* (2013.01)

(58) Field of Classification Search
CPC .. C07K 16/28; C07K 14/705; C12N 15/1037; C12N 15/1079; C12N 15/1093; A61K 38/00
See application file for complete search history.

(56) References Cited

U.S. PATENT DOCUMENTS

| 7,912,654 | B2 | 3/2011 | Kobilka et al. |
| 9,127,287 | B2 | 9/2015 | Hall et al. |
| 1,027,349 | A1 | 5/2019 | Mileni |
| 10,287,349 | B2 * | 5/2019 | Mileni ............... C07K 14/705 |
| 11,053,312 | B2 * | 7/2021 | Mileni ............... C12N 15/1093 |
| 2002/0045234 | A1 | 4/2002 | Squirrell et al. |
| 2004/0091975 | A1 | 5/2004 | Midoh et al. |
| 2004/0214317 | A1 | 10/2004 | Battaglino et al. |
| 2004/0265274 | A1 | 12/2004 | Wei et al. |
| 2006/0275288 | A1 | 12/2006 | Grihalde et al. |
| 2010/0099169 | A1 | 4/2010 | Bowie et al. |
| 2010/0304432 | A1 | 12/2010 | O'Keefe et al. |
| 2011/0028700 | A1 | 2/2011 | Heal et al. |
| 2011/0046351 | A1 | 2/2011 | Weir et al. |
| 2012/0270230 | A1 | 10/2012 | Henderson et al. |
| 2012/0302461 | A1 | 11/2012 | Camps et al. |
| 2013/0052646 | A1 | 2/2013 | Tripathi et al. |
| 2014/0256918 | A1 | 9/2014 | Chu et al. |

FOREIGN PATENT DOCUMENTS

| EP | 2450445 A1 | 5/2012 |
| WO | WO-2008068534 A2 | 6/2008 |
| WO | WO-2009081136 A2 | 7/2009 |
| WO | WO-2010078290 A2 | 7/2010 |
| WO | WO-2010149964 A2 | 12/2010 |
| WO | WO-2011033322 A2 | 3/2011 |
| WO | WO-2012022928 A2 | 2/2012 |
| WO | WO-2012098413 A1 | 7/2012 |
| WO | WO-2012120315 A2 | 9/2012 |
| WO | WO-2012137012 A1 | 10/2012 |
| WO | WO-2013021206 A2 | 2/2013 |
| WO | WO-2014026136 A2 | 2/2014 |
| WO | WO-2016070022 A1 | 5/2016 |
| WO | WO-2017192743 A1 | 11/2017 |

OTHER PUBLICATIONS

Brown et al. Pharmacology of GPR55 in Yeast and Identification of GSK494581A as a Mixed-Activity Glycine Transporter Subtype 1 Inhibitor and GPR55 Agonist. J Pharmacol Exp Ther 337:236-246 (2011).
Hibbert et al. Directed evolution strategies for improved enzymatic performance. Microb Cell Fact 4:29 (6 pgs.) (2005).
Hutchings et al. Monoclonal anti-β1-adrenergic receptor antibodies activate G protein signaling in the absence of β-arrestin recruitment. mAbs 6(1):246-261 (2014).
Klenk et al. A generic selection system for improved expression and thermostability of G protein-coupled receptors by directed evolution. Sci REp 6:21294 (2016).
Myers et al. A Yeast Genetic Screen Reveals a Critical Role for the Pore Helix Domain in TRP Channel Gating. Neuron 58:362-373 (2008).
PCT/US2015/58280 International Preliminary Report on Patentability dated May 11, 2017.

(Continued)

*Primary Examiner* — Daniel E Kolker
*Assistant Examiner* — James Ryland Melchior
(74) *Attorney, Agent, or Firm* — Viksnins Harris Padys Malen LLP

(57) ABSTRACT

In accordance with the present invention, there are provided functionally modulated tool receptors which are useful for drug discovery and development. In certain aspects and embodiments as described herein, a sophisticated and powerful approach has been designed that allows the rapid development of enhanced receptors, while simultaneously exploring millions of possibilities for improved properties with respect to such properties as protein expression, homogeneity, stabilization, conformational and activation pathway selectivity, antigenicity, immunogenicity, and the like. Indeed, the new methodology described herein represents a breakthrough by leveraging a full range of combinatorial amino acid replacements, in multiple positions simultaneously, in order to generate modified membrane-spanning proteins.

17 Claims, 4 Drawing Sheets

(56) References Cited

OTHER PUBLICATIONS

PCT/US2015/58280 International Search Report and Written Opinion dated Mar. 30, 2016.
PCT/US2017/030874 International Search Report and Written Opinion dated Jul. 27, 2017.
Sarkar et al. Directed evolution of a G protein-coupled receptor for expression, stability, and binding selectivity. PNAS USA 105:14808-14813 (2008).
Scarselli et al. Multiple Residues in the Second Extracellular Loop Are Critical for M3 Muscarinic Acetylcholine Receptor Activation. J Bio Chem 282:7385-7396 (2007).
Schlegel et al. Bacterial-based membrane protein production. Biochim Biophys Acta 1843(8):1739-1749 (2013).
Schlegel et al. Revolutionizing membrane protein overexpression in bacteria : Revolutionizing membrane protein overexpression in bacteria. Microbial Biotechnology 3(4):403-411 (2009).
Seitz et al. Enhancing the stability and solubility of the glucocorticoid receptor ligand-binding domain by high-throughput library screening. J Mol Biol 403:562-577 (2010).
Shibata et al. Thermostabilization of the neurotensin receptor NTS1. J Mol Biol 390:262-277 (2009).
Standfuss et al. Crystal structure of a thermally stable rhodopsin mutant. J Mol Biol 372:1179-1188 (2007).
U.S. Appl. No. 14/928,128 Office Action dated May 31, 2018.
U.S. Appl. No. 14/928,128 Office Action dated Nov. 1, 2017.
U.S. Appl. No. 16/098,821 Office Action dated Jan. 17, 2020.
Tucker, et al., "Purification of a rat neurotensin receptor expressed in *Escherichia coli*" Biochem. J. (1996) 891-899.
Skretas, et al., "Simple Genetic Selection Protocol for Isolation of Overexpressed Genes That Enhance Accumulation of Membrane-Integrated Human G Protein-Coupled Receptors in *Escherichia coli*" Applied and Environmental Microbiology (2010), vol. 76, No. 17, 5852-5859.
Jo, et al., "Engineering therapeutic antibodies targeting G-protein-coupled receptors" Experimental & Molecular Medicine (2016) p. 2-9.
Massey-Gendel, et al. "Genetic selection system for improving recombinant membrane protein expression in *E. coli*" Protein Science (2009) vol. 18, 372-383.

\* cited by examiner

MODIFIED MEMBRANE SPANNING PROTEINS AND METHODS FOR THE PREPARATION AND USE THEREOF

CROSS REFERENCE

This application is a continuation of U.S. patent application Ser. No. 16/411,059, filed May 13, 2019, which is a continuation of U.S. patent application Ser. No. 14/928,128, (now U.S. Pat. No. 10,287,349) filed Oct. 30, 2015, which claims the benefit of U.S. Provisional Application No. 62/073,554, filed Oct. 31, 2014, each of which application is incorporated herein by reference in their entirety.

FIELD OF THE INVENTION

The present disclosure relates to methods to modulate the functional properties of membrane-spanning proteins. In one aspect, the present disclosure relates to modified membrane-spanning proteins. In another aspect, the present disclosure relates to methods for the use of such modified membrane-spanning proteins.

BACKGROUND OF THE INVENTION

The information provided herein and references cited are provided solely to assist the understanding of the reader, and does not constitute an admission that any of the references or information is prior art to the present invention.

Membrane-spanning proteins such as G Protein Coupled Receptors (GPCRs) are among the most important classes of drug targets, currently targeted by about 30% of therapeutics in the market. However, the use of GPCRs for basic drug discovery and development in the pharmaceutical industry is inherently difficult due to the notoriously low expression, homogeneity, and stability thereof, and the high conformational flexibility of these integral membrane proteins, especially when removed from the cellular environment. This has greatly limited the success of protein-based approaches such as small molecule screening/assays and structural determination for structure-guided drug discovery, as well as antibody discovery efforts. These limitations remain to be addressed.

Importantly, only a very limited number of therapeutic antibodies targeting GPCRs have been approved, while most marketed therapeutics are small molecules or small peptides. As experienced often with non-GPCR targets, biologic drugs such as antibodies may enable access to a therapeutic space where small molecule drugs have failed. Therefore, the availability of GPCR-targeting antibodies will potentially facilitate previously unattainable opportunities for the betterment of human health.

SUMMARY OF THE INVENTION

In accordance with the present invention, the limitations of the art have been addressed through the generation of stabilized tool receptors for use in drug discovery and development.

Therefore, in certain aspects and embodiments as described herein, a sophisticated and powerful approach has been designed that allows the rapid development of enhanced receptors, while simultaneously exploring millions of possibilities for improved properties, such as increased protein expression, increased protein stability, increased protein homogeneity, increased protein antigenicity, increased protein immunogenicity, increased protein crystallizability, modulated conformational selectivity, modulated activation pathway selectivity, and the like. Indeed, the new methodology described herein represents a breakthrough by leveraging a full range of combinatorial amino acid replacements, in multiple positions simultaneously, in order to generate modified membrane-spanning proteins.

In addition, the efficiency of the readout system employed herein, i.e., the system by which clones are identified, is exponentially improved over current screening methods. Therefore, besides achieving higher protein expression and trafficking, the resulting membrane-spanning proteins (e.g., GPCRs) are characterized by having a greater spectrum of variation with respect to properties such as, for example, higher stability, a higher degree of conformational selectivity, and a higher degree of homogeneity), and the like. Therefore, modified membrane-spanning proteins, as described herein have great potential to aid the development of both biologics, small peptides and small molecule drugs.

DETAILED DESCRIPTION OF THE PREFERRED EMBODIMENTS

In accordance with the present invention, there are provided methods to modulate the functional properties of a membrane-spanning protein, said methods comprising:

generating a first polynucleotide library wherein a sufficient number of residues of a polynucleotide encoding said membrane-spanning protein are randomly modified so as to modulate the functional properties thereof, optionally generating a second polynucleotide library from said first polynucleotide library, said second polynucleotide library comprising a polynucleotide encoding said membrane-spanning protein modified by DNA shuffling in a sufficient number of amino acid residues so as to modulate the functional properties thereof, inserting the modified polynucleotides of said second polynucleotide library into a construct comprising:
  a signal sequence,
    a first marker sequence, wherein said first marker sequence is in-frame with said modified polynucleotide, and encodes one or more genes that overcome the sensitivity of said host to the presence of selective pressure agent(s)/conditions, and
    optionally a second marker sequence, wherein said second marker sequence, when present, is downstream of said signal sequence, but upstream of said modified polynucleotide,
  thereby producing modified polynucleotide-containing constructs,
transforming suitable host cells with the modified polynucleotide-containing constructs, and
selecting those cells which survive exposure to said selective pressure agent(s)/conditions and identifying the modified polynucleotide-containing construct(s) contained therein.

Figure 1:
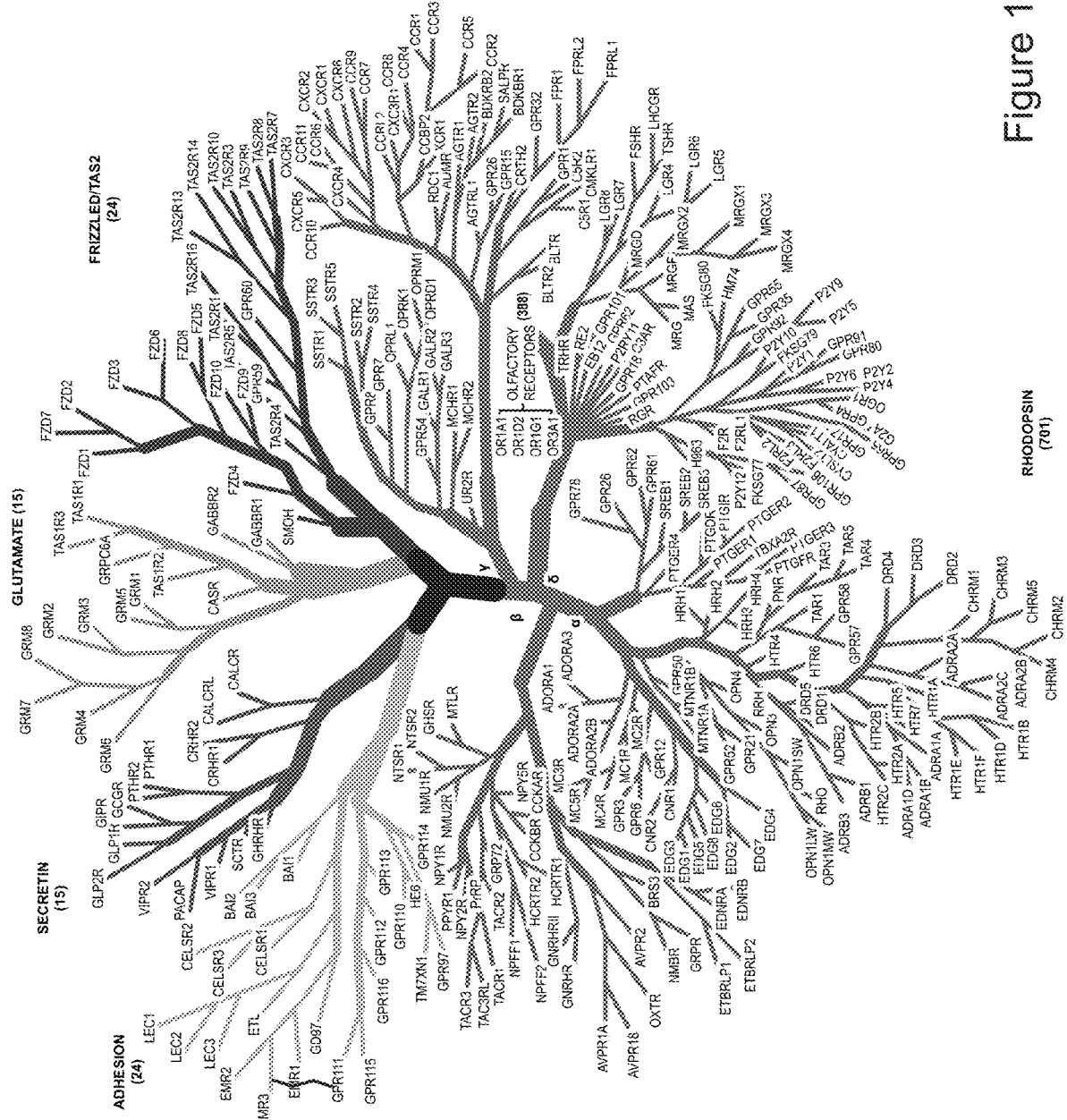
FIG. 1 is a GPCR family tree adopted from ihuman institute of Shanghai Tech.

As used herein, the phrase "membrane-spanning protein" refers to plasma membrane proteins, nuclear membrane proteins, peripheral membrane proteins, intracellular-membrane proteins (e.g. mitochondrial membrane proteins), transporters, channels, adhesins, translocases and receptors like G Protein Coupled Receptors (GPCRs) from all classes (A-F). Exemplary G-protein coupled receptors (GPCR) include adhesion receptors, secretins, glutamates, frizzled/TAS2, rhodopsin, olfactory receptors, and the like. See, for example, the GPCR family tree set forth in FIG. 1.

In generating a first polynucleotide library wherein a sufficient number of residues of a polynucleotide encoding said membrane-spanning protein (and the corresponding polypeptide sequence after translation thereof) are randomly modified so as to modulate the functional properties thereof, one typically modifies in the range of 1-50 residues; in some embodiments, one typically modifies 1-40 residues; in some embodiments, one typically modifies 1-30 residues; in some embodiments, one typically modifies 1-20 residues; in some embodiments, one typically modifies 1-15 residues; in some embodiments, one typically modifies 2-50 residues; in some embodiments, one typically modifies 2-40 residues; in some embodiments, one typically modifies 2-30 residues; in some embodiments, one typically modifies 2-20 residues; in some embodiments, one typically modifies 2-15 residues; in some embodiments, one typically modifies 3-50 residues; in some embodiments, one typically modifies 3-40 residues; in some embodiments, one typically modifies 3-30 residues; in some embodiments, one typically modifies 3-20 residues; in some embodiments, one typically modifies 3-15 residues; in some embodiments, one typically modifies 4-50 residues; in some embodiments, one typically modifies 4-40 residues; in some embodiments, one typically modifies 4-30 residues; in some embodiments, one typically modifies 4-20 residues; in some embodiments, one typically modifies 4-15 residues; in some embodiments, one typically modifies 5-50 residues; in some embodiments, one typically modifies 5-40 residues; in some embodiments, one typically modifies 5-30 residues; in some embodiments, one typically modifies 5-20 residues; in some embodiments, one typically modifies 5-15 residues; an average of 6 residues are modified (mutated) per 1 kB of DNA; in some embodiments, an average of 8 residues are modified (mutated) per 1 kB of DNA; in some embodiments, an average of 10 residues are modified (mutated) per 1 kB of DNA; in some embodiments, an average of 12 residues are modified (mutated) per 1 kB of DNA.

In optionally generating a second polynucleotide library from said first polynucleotide library, said second polynucleotide library comprising a polynucleotide encoding said membrane-spanning protein modified by DNA shuffling in a sufficient number of amino acid residues so as to modulate the functional properties thereof, one typically modifies 1-50 residues; in some embodiments, one typically modifies 1-40 residues; in some embodiments, one typically modifies 1-30 residues; in some embodiments, one typically modifies 1-20 residues; in some embodiments, one typically modifies 1-15 different amino acid residues per polynucleotide. In some embodiments, one typically modifies 2-50 residues; in some embodiments, one typically modifies 2-40 residues; in some embodiments, one typically modifies 2-30 residues; in some embodiments, one typically modifies 2-20 residues; in some embodiments, one typically modifies 2-15 different amino acid residues per polynucleotide; in some embodiments, one typically modifies 3-50 residues; in some embodiments, one typically modifies 3-40 residues; in some embodiments, one typically modifies 3-30 residues; in some embodiments, one typically modifies 3-20 residues; in some embodiments, one typically modifies 3-15 different amino acid residues per polynucleotide; in some embodiments, one typically modifies 4-50 residues; in some embodiments, one typically modifies 4-40 residues; in some embodiments, one typically modifies 4-30 residues; in some embodiments, one typically modifies 4-20 residues; in some embodiments, one typically modifies 4-15 different amino acid residues per polynucleotide; in some embodiments, one typically modifies 5-50 residues; in some embodiments, one typically modifies 5-40 residues; in some embodiments, one typically modifies 5-30 residues; in some embodiments, one typically modifies 5-20 residues; in some embodiments, one typically modifies 5-15 different amino acid residues per polynucleotide.

As used herein, "signal sequence" refers to a sequence of amino acid residues in the amino terminus of a nascent protein during protein translation, which when recognized by the signal recognition particle results in the transport of the nascent protein via the translocation pathway of the host organism.

Marker sequences contemplated for use herein encode one or more genes that overcome the sensitivity of said host to the presence of selective pressure agent(s) and/or selective pressure conditions. Exemplary marker sequences include ampicillin, chloramphenicol, neomycin, kanamycin, tetracycline, gentamicin resistance genes; pyrE gene (orotate phosphoribosyltransferase) and pyrF gene (orotidine-5'-monophosphate decarboxylase); URA3 gene (orotidine 5'-phosphate decarboxylase); LYS2 gene (alpha-aminoadipate reductase); ADE1-2 genes (phosphoribosylamino-imidazole-succinocarbozamide synthetase, phosphoribosylamino-imidazole-carboxylase), and the like.

Selective pressure agents/conditions refer to agents (including conditions) of differential mortality or fertility that tend to make a population change genetically. Exemplary selective pressure agents include antibiotics (e.g., ampicillin, carbenicillin, gentamicin, chloramphenicol, neomycin, kanamycin, tetracycline, and the like), toxic metabolites (e.g., 5-fluoroorotic acid or uracyl), conditions such as lack of nutrients for auxotrophic strains, and the like.

Exemplary selective pressure conditions include elevated temperature, reduced temperature, lack of necessary nutrient(s), co-factors, and the like. Exemplary nutrients include oxygen, carbon dioxide, and the like.

Other marker sequences contemplated for use herein encode reporter genes that confer traits that can be easily identified and measured in organisms expressing same.

Exemplary marker sequences include beta-galactosidase, alkaline phosphatase, green fluorescent protein, red fluorescent protein, tdTomato fluorescent protein, luciferase, and the like.

Inserting genetic material into suitable host cells with the modified polynucleotide-containing constructs described herein can be carried out in a variety of ways, e.g., by transformation or transfection, the process by which nucleic acids are introduced into bacteria or mammalian cells, respectively. Protocols and techniques vary widely and include lipid transfection and chemical and physical methods such as electroporation.

A variety of techniques suitable to employ for selecting cells which survive exposure to the selective pressure agent(s)/conditions are well known in the art (e.g. cell growth on agar plates), as are methods for identifying the modified polynucleotide-containing construct(s) contained therein according to the present invention (e.g. the Sanger polynucleotide sequencing method).

In some embodiments of the present invention, the functional property(ies) of a membrane-spanning protein are selected from the expression level of said membrane-spanning protein, the stability of said membrane-spanning protein, the conformational selectivity of said membrane-spanning protein, the homogeneity of said membrane-spanning protein, the crystallizability of said membrane-spanning protein, the antigenicity of said membrane-spanning protein, the immunogenicity of said membrane-spanning protein, the activation pathway selectivity of said membrane-spanning protein, and the like.

In some embodiments of the present invention, additional assays are carried out to verify the occurrence of membrane-spanning proteins having modulated functional properties. Such verification can be carried out, for example, by:

inserting the modified polynucleotide into suitable host cells, expressing said modified polynucleotide, and characterizing the resulting protein.

As readily recognized by those of skill in the art, a variety of characterization techniques and protocols are available to assess the various properties of the membrane proteins developed employing invention methods, e.g., homogeneity estimation and thermal denaturation assays, analytical size exclusion chromatography (SEC) or fluorescent SEC or fluorescent dyes; gel electrophoresis; direct binding measurements (including radioligand binding assays and surface plasmon resonance); signal transduction measurements (including cAMP production and calcium flux assays); and the like.

In some embodiments of the present invention, additional assays are carried out to identify the minimum working set of mutations required to achieve the desired modulated functional properties. Such evaluation can be carried out, for example, by:

randomly reverting said modified residues back, re-selecting in the presence of selective pressure agent(s)/conditions (e.g., antibiotic-containing medium), and re-characterizing (the modulated functional properties) in order to identify the minimum working set of mutations.

As readily recognized by those of skill in the art, a variety of host cells are suitable for use in the invention methods. Exemplary host cells are typically characterized by one or more of the following criteria:

being able to undergo transfection, transformation etc to receive (exogenous) genetic material (DNA, mRNA, plasmids, bacmids etc.);

being able to receive a limited number of copies of genetic material;

being able to form colonies or clonal biomass (genetically uniform);

possessing one or more selection markers (e.g., antibiotics, auxotrophies, toxins);

being able to effectively produce transmembrane proteins;

possessing the appropriate cellular machinery for translocation of proteins to the membrane environment; and/or being able to grow in mesophilic, thermophilic, hyperthermophilic and/or other extreme conditions.

Suitable host cells contemplated for use herein can be selected from the group consisting of bacterial cell lines, yeast cell lines, insect cell lines, mammalian cell lines, and the like.

Exemplary bacterial cell lines include, for example, *Escherichia coli, Bacillus subtilis, Baccillus brevis, Bacillus megaterium, Pseudomonas fluorescens, Thermus thermophilus, Aeropyrum pernix, Corynebacterium glutamicum, Sulfolobus islandicus,* and the like.

Exemplary yeast cell lines include, for example, *Pichia methanolica, Pichia angusta, Pichia thermomethanolica, Pichia pastoris, Saccharomyces cerevisiae, Schizosaccharomyces pombe, Arxula adeninivorans, Kluyveromyces lactis, Yarrowia hpolytica,* and the like.

Exemplary mammalian cell lines include, for example, Embryonic Kidney cells (Human), *Bos primigenius* (Bovine), *Mus musculus* (Mouse), *Cricetulus griseus* (Chinese Hamster Ovary), Baby Hamster Kidney, and the like.

Exemplary insect cells include, for example, *Spodoptera frupperda, Trichoplusia ni,* and the like.

In accordance with yet another embodiment of the present invention, there are provided modified membrane-spanning proteins identified by the above-described methods. Typically, said modified membrane-spanning protein have one or more improved functional properties relative to the wild type membrane-spanning protein.

In accordance with still another embodiment of the present invention, there are provided methods to modulate the functional properties of a membrane-spanning protein, said method comprising:

generating a polynucleotide library wherein a sufficient number of bases of a polynucleotide encoding said membrane-spanning protein and/or a sufficient number of amino acid residues of said membrane-spanning protein are randomly modified so as to modulate the functional properties thereof, inserting the modified polynucleotides of said second polynucleotide library into a construct comprising:

a signal sequence, and a first marker sequence, wherein said marker sequence is in-frame with said modified polynucleotide, and encodes one or more genes that overcome the sensitivity of said host to the presence of selective pressure agent(s)/conditions, optionally a second marker sequence, wherein said second marker sequence, when present, is downstream of said signal sequence, but upstream of said modified polynucleotide, thereby producing modified polynucleotide-containing constructs, transforming suitable host cells with the modified polynucleotide-containing constructs, and selecting those cells which survive exposure to said selective pressure agent(s)/conditions (e.g., antibiotic)

and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein.

In accordance with yet another embodiment of the present invention, there are provided methods to modulate the functional properties of a membrane-spanning protein, said methods comprising:
    inserting each member of a modified polynucleotide library into a construct, wherein a sufficient number of bases of a polynucleotide encoding said membrane-spanning protein and/or a sufficient number of amino acid residues of said membrane-spanning protein are randomly modified so as to modulate the functional properties thereof, said construct comprising:
        a signal sequence, and
        a first marker sequence, wherein said marker sequence is in-frame with said modified polynucleotide, and encodes one or more genes that overcome the sensitivity of said host to the presence of selective pressure agent(s)/conditions, and
        optionally a second marker sequence, wherein said second marker sequence, when present, is downstream of said signal sequence, but upstream of said modified polynucleotide,
    thereby producing modified polynucleotide-containing constructs,
    transforming suitable host cells with the modified polynucleotide-containing constructs, and
    selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein.

In accordance with a further embodiment of the present invention, there are provided methods to modulate the functional properties of a membrane-spanning protein, said method comprising:
    transforming suitable host cells with a construct comprising:
        a modified polynucleotide,
        a signal sequence, and
        one or more marker sequences,
    wherein:
        said marker sequence is in-frame with said modified polynucleotide, and encodes one or more genes that overcome the sensitivity of said host to the presence of selective pressure agent(s)/conditions,
        said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to modulate the functional properties thereof, and optionally thereafter
    generating a second library from said first library, said second library comprising a polynucleotide encoding said membrane-spanning protein randomly modified in a sufficient number of amino acid residues so as to modulate the functional properties thereof, and
    selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein.

In accordance with yet another embodiment of the present invention, there are provided methods to modulate the functional properties of a membrane-spanning protein, said methods comprising selecting those cells which survive exposure to selective pressure agent(s)/conditons (e.g., antibiotic) and identifying the modified polynucleotide-containing construct(s) contained therein, wherein said cells are transformed with:
    a modified polynucleotide,
    a signal sequence, and
    one or more marker sequences,
    wherein:
        said marker sequence is in-frame with said modified polynucleotide, and encodes one or more genes that overcome the sensitivity of said host to the presence of selective pressure agent(s)/conditions,
        said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to modulate the functional properties thereof, and optionally thereafter
    generating a second library from said first library, said second library comprising a polynucleotide encoding said membrane-spanning protein randomly modified in a sufficient number of amino acid residues so as to modulate the functional properties thereof.

In accordance with yet another embodiment of the present invention, there are provided modified membrane-spanning proteins identified by the above-described methods. Typically, said modified membrane-spanning protein have one or more improved functional properties relative to the wild type membrane-spanning protein.

In certain aspects of the present invention , wherein the property to be modulated is the stability of said membrane-spanning protein, the invention method comprises:
    generating a first polynucleotide library wherein a sufficient number of bases of a polynucleotide encoding said membrane-spanning protein and/or a sufficient number of amino acid residues of said membrane-spanning protein are randomly modified so as to modulate the stability thereof,
    optionally generating a second polynucleotide library from said first polynucleotide library, said second polynucleotide library comprising a polynucleotide encoding said membrane-spanning protein modified by DNA shuffling in a sufficient number of amino acid residues so as to modulate the stability thereof, inserting the modified polynucleotides of said second
polynucleotide library into a construct comprising:
a signal sequence,
a first marker sequence, wherein said first marker
sequence is in-frame with said modified polynucleotide, and encodes one or more genes that overcome
the sensitivity of said host to the presence of selective pressure agent(s)/conditions, and
optionally a second marker sequence, wherein said
second marker sequence, when present, is downstream of said signal sequence, but upstream of said
modified polynucleotide,
thereby producing modified polynucleotide-containing
constructs,
transforming suitable host cells with the modified polynucleotide-containing constructs, and
selecting those cells which survive exposure to said
selective pressure agent(s)/conditions (e.g., antibiotic)
and identifying the modified polynucleotide-containing
construct(s) contained therein.

Suitable host cells contemplated for use in this aspect of
the present invention can be selected from the group consisting of bacterial cell lines, yeast cell lines, insect cell
lines, and mammalian cell lines.

In accordance with yet another embodiment of the present
invention, there are provided modified membrane-spanning
proteins identified by the above-described methods. Typically, said modified membrane-spanning protein have one or
more improved functional properties relative to the wild
type membrane-spanning protein, e.g., increased stability
relative to wild type.

In accordance with still another embodiment of the present invention, there are provided methods to modulate the
stability of a membrane-spanning protein, said method comprising:
generating a polynucleotide library wherein a sufficient
number of bases of a polynucleotide encoding said
membrane-spanning protein and/or a sufficient number
of amino acid residues of said membrane-spanning
protein are randomly modified so as to modulate the
stability thereof,
inserting the modified polynucleotides of said second
polynucleotide library into a construct comprising:
a signal sequence, and
a first marker sequence, wherein said marker sequence
is in-frame with said modified polynucleotide, and
encodes one or more genes that overcome the sensitivity of said host to the presence of selective
pressure agent(s)/conditions, and
optionally a second marker sequence, wherein said
second marker sequence, when present, is downstream of said signal sequence, but upstream of said
modified polynucleotide,
thereby producing modified polynucleotide-containing
constructs,
transforming suitable host cells with the modified polynucleotide-containing constructs, and
selecting those cells which survive exposure to said
selective pressure agent(s)/conditions (e.g., antibiotic)
and identifying the modified polynucleotide-containing
construct(s) contained therein.

In accordance with yet another embodiment of the present
invention, there are provided modified membrane-spanning
proteins identified by the above-described methods. Typically, said modified membrane-spanning protein have one or
more improved functional properties relative to the wild
type membrane-spanning protein, e.g., increased stability
relative to wild type.

In accordance with yet another embodiment of the present
invention, there are provided methods to modulate the
stability of a membrane-spanning protein, said methods
comprising:
inserting each member of a modified polynucleotide
library into a construct, wherein a sufficient number of
bases of a polynucleotide encoding said membrane-spanning protein and/or a sufficient number of amino
acid residues of said membrane-spanning protein are
randomly modified so as to modulate the stability
thereof, said construct comprising:
a signal sequence, and
a first marker sequence, wherein said marker sequence
is in-frame with said modified polynucleotide, and
encodes one or more genes that overcome the sensitivity of said host to the presence of selective
pressure agent(s)/conditions, and
optionally a second marker sequence, wherein said
second marker sequence, when present, is downstream of said signal sequence, but upstream of said
modified polynucleotide,
thereby producing modified polynucleotide-containing
constructs,
transforming suitable host cells with the modified polynucleotide-containing constructs, and
selecting those cells which survive exposure to said
selective pressure agent(s)/conditions (e.g., antibiotic)
and identifying the modified polynucleotide-containing
construct(s) contained therein.

In accordance with yet another embodiment of the present
invention, there are provided modified membrane-spanning
proteins identified by the above-described methods. Typically, said modified membrane-spanning protein have one or
more improved functional properties relative to the wild
type membrane-spanning protein, e.g., increased stability
relative to wild type.

In accordance with a further embodiment of the present
invention, there are provided methods to modulate the
stability of a membrane-spanning protein, said method comprising:
transforming suitable host cells with a construct comprising:
a modified polynucleotide,
a signal sequence, and
one or more marker sequences,
wherein:
said marker sequence is in-frame with said modified
polynucleotide, and encodes one or more genes that
overcome the sensitivity of said host to the presence
of selective pressure agent(s)/conditions,
said modified polynucleotide is obtained by generating
a first polynucleotide library wherein a sufficient
number of bases of a polynucleotide encoding said
membrane-spanning protein and/or a sufficient number of amino acid residues of said membrane-spanning protein are randomly modified so as to increase
the stability thereof, and optionally thereafter
generating a second library from said first library, said
second library comprising a polynucleotide encoding
said membrane-spanning protein randomly modified in
a sufficient number of amino acid residues so as to
increase the stability thereof, and
selecting those cells which survive exposure to said
selective pressure agent(s)/conditions (e.g., antibiotic)

and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased stability relative to wild type.

In accordance with yet another embodiment of the present invention, there are provided methods to modulate the stability of a membrane-spanning protein, said methods comprising selecting those cells which survive exposure to selective pressure agent(s)/conditions (e.g., antibiotic) and identifying the modified polynucleotide-containing construct(s) contained therein, wherein said cells are transformed with:
  a modified polynucleotide,
  a signal sequence, and
  one or more marker sequences,
  wherein:
    said marker sequence(s) is/are in-frame with said modified polynucleotide, and encodes one or more genes that overcome the sensitivity of said host to the presence of selective pressure agent(s)/conditions,
    said modified polynucleotide is obtained by generating a first polynucleotide library wherein a sufficient number of bases of a polynucleotide encoding said membrane-spanning protein are randomly modified so as to modulate the stability of said membrane-spanning protein, and thereafter optionally
    generating a second library from said first library, said second library comprising a polynucleotide encoding said membrane-spanning protein randomly modified in a sufficient number of amino acid residues so as to increase the stability thereof.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased stability relative to wild type.

In certain aspects of the present invention, wherein the property to be modulated is the homogeneity of a membrane-spanning protein, the invention method comprises:
  generating a first polynucleotide library wherein a sufficient number of bases of a polynucleotide encoding said membrane-spanning protein and/or a sufficient number of amino acid residues of said membrane-spanning protein are randomly modified so as to increase the homogeneity thereof,
  optionally generating a second polynucleotide library from said first polynucleotide library, said second polynucleotide library comprising a polynucleotide encoding said membrane-spanning protein modified by DNA shuffling in a sufficient number of amino acid residues so as to increase the homogeneity thereof,
  inserting the modified polynucleotides of said second polynucleotide library into a construct comprising:
    a signal sequence,
    a first marker sequence, wherein said first marker sequence is in-frame with said modified polynucleotide, and encodes one or more genes that overcome the sensitivity of said host to the presence of selective pressure agent(s)/conditions, and
    optionally a second marker sequence, wherein said second marker sequence, when present, is downstream of said signal sequence, but upstream of said modified polynucleotide,
  thereby producing modified polynucleotide-containing constructs,
  transforming suitable host cells with the modified polynucleotide-containing constructs, and
  selecting those cells which survive exposure to said selective pressure agent(s)/conditions, (e.g., an antibiotic) and identifying the modified polynucleotide-containing construct(s) contained therein.

Suitable host cells contemplated for use in this aspect of the present invention can be selected from the group consisting of bacterial cell lines, yeast cell lines, insect cell lines, and mammalian cell lines.

In accordance with yet another embodiment of the present invention, there are provided modified membrane-spanning proteins identified by the above-described methods. Typically, said modified membrane-spanning proteins have one or more improved functional properties relative to the wild type membrane-spanning protein, e.g., increased homogeneity relative to wild type.

In accordance with still another embodiment of the present invention, there are provided methods to modulate the homogeneity of a membrane-spanning protein, said method comprising:
  generating a polynucleotide library wherein a sufficient number of bases of a polynucleotide encoding said membrane-spanning protein and/or a sufficient number of amino acid residues of said membrane-spanning protein are randomly modified so as to increase the homogeneity thereof,
  inserting the modified polynucleotides of said second polynucleotide library into a construct comprising:
    a signal sequence, and
    a first marker sequence, wherein said marker sequence is in-frame with said modified polynucleotide, and encodes one or more genes that overcome the sensitivity of said host to the presence of selective pressure agent(s)/conditions, and
    optionally a second marker sequence, wherein said second marker sequence, when present, is downstream of said signal sequence, but upstream of said modified polynucleotide,
  thereby producing modified polynucleotide-containing constructs,
  transforming suitable host cells with the modified polynucleotide-containing constructs, and
  selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased homogeneity relative to wild type.

In accordance with yet another embodiment of the present invention, there are provided methods to modulate the homogeneity of a membrane-spanning protein, said methods comprising:
  inserting each member of a modified polynucleotide library into a construct, wherein a sufficient number of bases of a polynucleotide encoding said membrane-spanning protein and/or a sufficient number of amino acid residues of said membrane-spanning protein are randomly modified so as to increase the homogeneity thereof, said construct comprising:
  a signal sequence, and
  a first marker sequence, wherein said marker sequence is in-frame with said modified polynucleotide, and encodes one or more genes that overcome the sensitivity of said host to the presence of selective pressure agent(s)/conditions, and
  optionally a second marker sequence, wherein said second marker sequence, when present, is downstream of said signal sequence, but upstream of said modified polynucleotide,
  thereby producing modified polynucleotide-containing constructs,
transforming suitable host cells with the modified polynucleotide-containing constructs, and
selecting those cells which survive exposure to said selective pressure agent/condition (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased homogeneity relative to wild type.

In accordance with a further embodiment of the present invention, there are provided methods to modulate the homogeneity of a membrane-spanning protein, said method comprising:
  transforming suitable host cells with a construct comprising:
    a modified polynucleotide,
    a signal sequence, and
    one or more marker sequences,
    wherein:
      said marker sequence(s) is/are in-frame with said modified polynucleotide, and encodes one or more genes that overcome the sensitivity of said host to the presence of selective pressure agent(s)/conditions,
      said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to increase the homogeneity thereof, and optionally thereafter
    generating a second library from said first library, said second library comprising a polynucleotide encoding said membrane-spanning protein randomly modified in a sufficient number of amino acid residues so as to increase the homogeneity thereof, and
  selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased homogeneity relative to wild type.

In accordance with yet another embodiment of the present invention, there are provided methods to modulate the homogeneity of a membrane-spanning protein, said methods comprising selecting those cells which survive exposure to selective pressure agent(s)/conditions (e.g., antibiotic) and identifying the modified polynucleotide-containing construct(s) contained therein, wherein said cells are transformed with:
  a modified polynucleotide,
  a signal sequence, and
  one or more marker sequence,
  wherein:
    said marker sequence(s) is/are in-frame with said modified polynucleotide, and encodes one or more genes that overcome the sensitivity of said host to the presence of selective pressure agent(s)/conditions,
    said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to increase the homogeneity thereof, and optionally thereafter
  generating a second library from said first library, said second library comprising a polynucleotide encoding said membrane-spanning protein randomly modified in a sufficient number of amino acid residues so as to increase the homogeneity thereof.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased homogeneity relative to wild type.

In certain aspects of the present invention, wherein the property to be modulated is the crystallizability of a membrane-spanning protein, the invention method comprises:
  generating a first polynucleotide library wherein a sufficient number of bases of a polynucleotide encoding said membrane-spanning protein and/or a sufficient number of amino acid residues of said membrane-spanning protein are randomly modified so as to increase the crystallizability thereof,
  optionally generating a second polynucleotide library from said first polynucleotide library, said second polynucleotide library comprising a polynucleotide encoding said membrane-spanning protein modified by DNA shuffling in a sufficient number of amino acid residues so as to increase the crystallizability thereof,
  inserting the modified polynucleotides of said second polynucleotide library into a construct comprising:
    a signal sequence,
    a first marker sequence, wherein said first marker sequence is in-frame with said modified polynucleotide, and encodes one or more genes that overcome the sensitivity of said host to the presence of selective pressure agent(s)/conditions, and
    optionally a second marker sequence, wherein said second marker sequence, when present, is downstream of said signal sequence, but upstream of said modified polynucleotide,
    thereby producing modified polynucleotide-containing constructs,
  transforming suitable host cells with the modified polynucleotide-containing constructs, and selecting those cells which survive exposure to said selective pressure agent(s)/conditions, (e.g., antibiotic) and identifying the modified polynucleotide-containing construct(s) contained therein.

Suitable host cells contemplated for use in this aspect of the present invention can be selected from the group consisting of bacterial cell lines, yeast cell lines, insect cell lines, and mammalian cell lines.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., higher crystallizability relative to wild type.

In accordance with still another embodiment of the present invention, there are provided methods to modulate the crystallizability of a membrane-spanning protein, said method comprising:
  generating a polynucleotide library wherein a sufficient number of bases of a polynucleotide encoding said membrane-spanning protein and/or a sufficient number of amino acid residues of said membrane-spanning protein are randomly modified so as to increase the crystallizability thereof,
  inserting the modified polynucleotides of said second polynucleotide library into a construct comprising:
    a signal sequence, and
    a first marker sequence, wherein said marker sequence is in-frame with said modified polynucleotide, and encodes one or more genes that overcome the sensitivity of said host to the presence of selective pressure agent(s)/conditions, and
    optionally a second marker sequence, wherein said second marker sequence, when present, is downstream of said signal sequence, but upstream of said modified polynucleotide,
  thereby producing modified polynucleotide-containing constructs,
  transforming suitable host cells with the modified polynucleotide-containing constructs, and
  selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., higher crystallizability relative to wild type.

In accordance with yet another embodiment of the present invention, there are provided methods to modulate the crystallizability of a membrane-spanning protein, said methods comprising:
  inserting each member of a modified polynucleotide library into a construct, wherein a sufficient number of bases of a polynucleotide encoding said membrane-spanning protein and/or a sufficient number of amino acid residues of said membrane-spanning protein are randomly modified so as to increase the crystallizability thereof, said construct comprising:
    a signal sequence, and
    a first marker sequence, wherein said marker sequence is in-frame with said modified polynucleotide, and encodes one or more genes that overcome the sensitivity of said host to the presence of selective pressure agent(s)/conditions, and
    optionally a second marker sequence, wherein said second marker sequence, when present, is downstream of said signal sequence, but upstream of said modified polynucleotide,
  thereby producing modified polynucleotide-containing constructs,
  transforming suitable host cells with the modified polynucleotide-containing constructs, and
  selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., higher crystallizability relative to wild type.

In accordance with a further embodiment of the present invention, there are provided methods to modulate the crystallizability of a membrane-spanning protein, said method comprising:
  transforming suitable host cells with a construct comprising:
    a modified polynucleotide,
    a signal sequence, and
    one or more marker sequence(s),
  wherein:
    said marker sequence is in-frame with said modified polynucleotide, and encodes one or more genes that overcome the sensitivity of said host to the presence of selective pressure agent(s)/conditions,
    said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to increase the crystallizability thereof, and optionally thereafter generating a second library from said first library, said second library comprising a polynucleotide encoding said membrane-spanning protein randomly modified in a sufficient number of amino acid residues so as to increase the crystallizability thereof, and
  selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., higher crystallizability relative to wild type.

In accordance with yet another embodiment of the present invention, there are provided methods to modulate the crystallizability of a membrane-spanning protein, said methods comprising selecting those cells which survive exposure to selective pressure agent(s)/conditions (e.g., antibiotic) and identifying the modified polynucleotide-containing construct(s) contained therein, wherein said cells are transformed with:
a modified polynucleotide,
a signal sequence, and
one or more marker sequence(s),
wherein:
said marker sequence(s) is/are in-frame with said modified polynucleotide, and encodes one or more genes that overcome the sensitivity of said host to the presence of selective pressure agent(s)/conditions,
said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to increase the crystallizability thereof, and optionally thereafter
generating a second library from said first library, said second library comprising a polynucleotide encoding said membrane-spanning protein randomly modified in a sufficient number of amino acid residues so as to increase the crystallizability thereof In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., higher crystallizability relative to wild type.

In certain aspects of the present invention, wherein the property to be modulated is the antigenicity of a membrane-spanning protein, the invention method comprises:
generating a first polynucleotide library wherein a sufficient number of bases of a polynucleotide encoding said membrane-spanning protein and/or a sufficient number of amino acid residues of said membrane-spanning protein are randomly modified so as to increase the antigenicity thereof,
generating a second library from said first library, said second library comprising a polynucleotide encoding said membrane-spanning protein modified by DNA shuffling in a sufficient number of amino acid residues so as to increase the antigenicity thereof,
inserting the resultant modified genes into a construct comprising:
a signal sequence,
a first marker sequence, wherein said first marker sequence is in-frame with said modified polynucleotide, and encodes one or more genes that overcome the sensitivity of said host to the presence of selective pressure agent(s)/conditions, and
optionally a second marker sequence, wherein said second marker sequence, when present, is downstream of said signal sequence, but upstream of said modified polynucleotide,
transforming suitable host cells with the resulting constructs, and
selecting those cells which survive exposure to said selective pressure agent(s)/conditions (e.g., antibiotic) and identifying the modified polynucleotide-containing construct(s) contained therein.

Suitable host cells contemplated for use in this aspect of the present invention can be selected from the group consisting of bacterial cell lines, yeast cell lines, insect cell lines, and mammalian cell lines.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased antigenicity relative to wild type.

In accordance with still another embodiment of the present invention, there are provided methods to modulate the antigenicity of a membrane-spanning protein, said method comprising:
generating a polynucleotide library wherein a sufficient number of bases of a polynucleotide encoding said membrane-spanning protein and/or a sufficient number of amino acid residues of said membrane-spanning protein are randomly modified so as to increase the antigenicity thereof,
inserting the modified polynucleotides of said second polynucleotide library into a construct comprising:
a signal sequence, and
a first marker sequence, wherein said marker sequence is in-frame with said modified polynucleotide, and encodes one or more genes that overcome the sensitivity of said host to the presence of selective pressure agent(s)/conditions, and
optionally a second marker sequence, wherein said second marker sequence, when present, is downstream of said signal sequence, but upstream of said modified polynucleotide,
thereby producing modified polynucleotide-containing constructs,
transforming suitable host cells with the modified polynucleotide-containing constructs, and
selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased antigenicity relative to wild type.

In accordance with yet another embodiment of the present invention, there are provided methods to modulate the antigenicity of a membrane-spanning protein, said methods comprising:
inserting each member of a modified polynucleotide library into a construct, wherein a sufficient number of bases of a polynucleotide encoding said membrane-spanning protein and/or a sufficient number of amino acid residues of said membrane-spanning protein are randomly modified so as to increase the antigenicity thereof, said construct comprising:
a signal sequence, and
a first marker sequence, wherein said marker sequence is in-frame with said modified polynucleotide, and encodes one or more genes that overcome the sensitivity of said host to the presence of selective pressure agent(s)/conditions, and
optionally a second marker sequence, wherein said second marker sequence, when present, is downstream of said signal sequence, but upstream of said modified polynucleotide,
thereby producing modified polynucleotide-containing constructs,
transforming suitable host cells with the modified polynucleotide-containing constructs, and selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased antigenicity relative to wild type.

In accordance with a further embodiment of the present invention, there are provided methods to modulate the antigenicity of a membrane-spanning protein, said method comprising:
transforming suitable host cells with a construct comprising:
a modified polynucleotide,
a signal sequence, and
one or more marker sequence(s),
wherein:
said marker sequence(s) is/are in-frame with said modified polynucleotide, and encodes one or more genes that overcome the sensitivity of said host to the presence of selective pressure agent(s)/conditions,
said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to increase the antigenicity thereof, and optionally thereafter
generating a second library from said first library, said second library comprising a polynucleotide encoding said membrane-spanning protein randomly modified in a sufficient number of amino acid residues so as to increase the antigenicity thereof, and
selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased antigenicity relative to wild type.

In accordance with yet another embodiment of the present invention, there are provided methods to modulate the antigenicity of a membrane-spanning protein, said methods comprising selecting those cells which survive exposure to selective pressure agent(s)/conditions (e.g., antibiotic) and identifying the modified polynucleotide-containing construct(s) contained therein, wherein said cells are transformed with:
a modified polynucleotide,
a signal sequence, and
one or more marker sequence(s),
wherein:
said marker sequence(s) is/are in-frame with said modified polynucleotide, and encodes one or more genes that overcome the sensitivity of said host to the presence of selective pressure agent(s)/conditions,
said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to increase the antigenicity thereof, and optionally thereafter
generating a second library from said first library, said second library comprising a polynucleotide encoding said membrane-spanning protein randomly modified in a sufficient number of amino acid residues so as to increase the antigenicity thereof In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased antigenicity relative to wild type.

In certain aspects of the present invention, wherein the property to be modulated is the immunogenicity of a membrane-spanning protein, the invention method comprises:
generating a first polynucleotide library wherein a sufficient number of bases of a polynucleotide encoding said membrane-spanning protein and/or a sufficient number of amino acid residues of said membrane-spanning protein are randomly modified so as to increase the immunogenicity thereof,
generating a second library from said first library, said second library comprising a polynucleotide encoding said membrane-spanning protein modified by DNA shuffling in a sufficient number of amino acid residues so as to increase the immunogenicity thereof,
inserting the resultant modified genes into a construct comprising:
a signal sequence,
a first marker sequence, wherein said first marker sequence is in-frame with said modified polynucleotide, and encodes one or more genes that overcome the sensitivity of said host to the presence of selective pressure agent(s)/conditions, and
optionally a second marker sequence, wherein said second marker sequence, when present, is downstream of said signal sequence, but upstream of said modified polynucleotide,
transforming suitable host cells with the resulting constructs, and
selecting those cells which survive exposure to said selective pressure agent(s)/conditions (e.g., antibiotic) and identifying the modified polynucleotide-containing construct(s) contained therein.

Suitable host cells contemplated for use in this aspect of the present invention can be selected from the group consisting of bacterial cell lines, yeast cell lines, insect cell lines, and mammalian cell lines.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased immunogenicity relative to wild type.

In accordance with still another embodiment of the present invention, there are provided methods to modulate the immunogenicity of a membrane-spanning protein, said method comprising:
generating a polynucleotide library wherein a sufficient number of bases of a polynucleotide encoding said membrane-spanning protein and/or a sufficient number of amino acid residues of said membrane-spanning protein are randomly modified so as to increase the immunogenicity thereof, inserting the modified polynucleotides of said second polynucleotide library into a construct comprising:
a signal sequence, and
a first marker sequence, wherein said marker sequence is in-frame with said modified polynucleotide, and encodes one or more genes that overcome the sensitivity of said host to the presence of selective pressure agent(s)/conditions, and
optionally a second marker sequence, wherein said second marker sequence, when present, is downstream of said signal sequence, but upstream of said modified polynucleotide,
thereby producing modified polynucleotide-containing constructs,
transforming suitable host cells with the modified polynucleotide-containing constructs, and
selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased immunogenicity relative to wild type.

In accordance with yet another embodiment of the present invention, there are provided methods to modulate the immunogenicity of a membrane-spanning protein, said methods comprising:
inserting each member of a modified polynucleotide library into a construct, wherein a sufficient number of bases of a polynucleotide encoding said membrane-spanning protein and/or a sufficient number of amino acid residues of said membrane-spanning protein are randomly modified so as to increase the immunogenicity thereof, said construct comprising:
a signal sequence, and
a first marker sequence, wherein said marker sequence is in-frame with said modified polynucleotide, and encodes one or more genes that overcome the sensitivity of said host to the presence of selective pressure agent(s)/conditions, and
optionally a second marker sequence, wherein said second marker sequence, when present, is downstream of said signal sequence, but upstream of said modified polynucleotide,
thereby producing modified polynucleotide-containing constructs,
transforming suitable host cells with the modified polynucleotide-containing constructs, and
selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased immunogenicity relative to wild type.

In accordance with a further embodiment of the present invention, there are provided methods to modulate the immunogenicity of a membrane-spanning protein, said method comprising:
transforming suitable host cells with a construct comprising:
a modified polynucleotide,
a signal sequence, and
one or more marker sequence(s),
wherein:
said marker sequence(s) is/are in-frame with said modified polynucleotide, and encodes one or more genes that overcome the sensitivity of said host to the presence of selective pressure agent(s)/conditions,
said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to increase the immunogenicity thereof, and optionally thereafter
generating a second library from said first library, said second library comprising a polynucleotide encoding said membrane-spanning protein randomly modified in a sufficient number of amino acid residues so as to increase the immunogenicity thereof, and
selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased immunogenicity relative to wild type.

In accordance with yet another embodiment of the present invention, there are provided methods to modulate the immunogenicity of a membrane-spanning protein, said methods comprising selecting those cells which survive exposure to selective pressure agent(s)/conditions (e.g., antibiotic) and identifying the modified polynucleotide-containing construct(s) contained therein, wherein said cells are transformed with:
a modified polynucleotide,
a signal sequence, and
one or more marker sequence(s),
wherein:
said marker sequence(s) is/are in-frame with said modified polynucleotide, and encodes one or more genes that overcome the sensitivity of said host to the presence of selective pressure agent(s)/conditions,
said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to increase the immunogenicity thereof, and optionally thereafter
generating a second library from said first library, said second library comprising a polynucleotide encoding said membrane-spanning protein randomly modified in a sufficient number of amino acid residues so as to increase the immunogenicity thereof.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., increased immunogenicity relative to wild type.

In certain aspects of the present invention, wherein the property to be modulated is the conformational selectivity and/or activation pathway selectivity of a membrane-spanning protein, the invention method comprises:

generating a first polynucleotide library wherein a sufficient number of bases of a polynucleotide encoding said membrane-spanning protein and/or a sufficient number of amino acid residues of said membrane-spanning protein are randomly modified so as to modulate the conformational selectivity and/or activation pathway selectivity thereof, generating a second library from said first library, said second library comprising a polynucleotide encoding said membrane-spanning protein modified by DNA shuffling in a sufficient number of amino acid residues so as to modulate the conformational selectivity and/or activation pathway selectivity thereof, inserting the resultant modified genes into a construct comprising:
a signal sequence,
a first marker sequence, wherein said first marker sequence is in-frame with said modified polynucleotide, and encodes one or more genes that overcome the sensitivity of said host to the presence of selective pressure agent(s)/conditions, and
optionally a second marker sequence, wherein said second marker sequence, when present, is downstream of said signal sequence, but upstream of said modified polynucleotide, transforming suitable host cells with the resulting constructs, and
- selecting those cells which survive exposure to said selective pressure agent(s)/conditions (e.g., antibiotic) and identifying the modified polynucleotide-containing construct(s) contained therein.

As used herein, "conformational selectivity" refers to the activity profile of a polypeptide as a function of the conformation thereof. For example, certain conformations of a peptide or protein may be more or less susceptible to binding or activating other proteins, peptides or compounds. In certain embodiments and aspects, the conformational selectivity embraces samples for which the conformation thereof is substantially homogeneous.

As used herein, "activation pathway selectivity" refers to the ability of an agent to selectively activate one or a limited number of metabolic or signaling pathways from among a plurality of available metabolic or signaling pathways.

Suitable host cells contemplated for use in this aspect of the present invention can be selected from the group consisting of bacterial cell lines, yeast cell lines, insect cell lines, and mammalian cell lines.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., modulated conformational selectivity and/or activation pathway selectivity relative to wild type.

In accordance with still another embodiment of the present invention, there are provided methods to modulate the conformational selectivity and/or activation pathway selectivity of a membrane-spanning protein, said method comprising:

- generating a polynucleotide library wherein a sufficient number of bases of a polynucleotide encoding said membrane-spanning protein and/or a sufficient number of amino acid residues of said membrane-spanning protein are randomly modified so as to modulate the conformational selectivity and/or activation pathway selectivity thereof,
- inserting the modified polynucleotides of said second polynucleotide library into a construct comprising:
  - a signal sequence, and
  - a first marker sequence, wherein said marker sequence is in-frame with said modified polynucleotide, and encodes one or more genes that overcome the sensitivity of said host to the presence of selective pressure agent(s)/conditions, and
  - optionally a second marker sequence, wherein said second marker sequence, when present, is downstream of said signal sequence, but upstream of said modified polynucleotide,
  - thereby producing modified polynucleotide-containing constructs,
- transforming suitable host cells with the modified polynucleotide-containing constructs, and
- selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., modulated conformational selectivity and/or activation pathway selectivity relative to wild type.

In accordance with yet another embodiment of the present invention, there are provided methods to modulate the conformational selectivity and/or activation pathway selectivity of a membrane-spanning protein, said methods comprising:

- inserting each member of a modified polynucleotide library into a construct, wherein a sufficient number of bases of a polynucleotide encoding said membrane-spanning protein and/or a sufficient number of amino acid residues of said membrane-spanning protein are randomly modified so as to modulate the conformational selectivity and/or activation pathway selectivity thereof, said construct comprising:
  - a signal sequence, and
  - a first marker sequence, wherein said marker sequence is in-frame with said modified polynucleotide, and encodes one or more genes that overcome the sensitivity of said host to the presence of selective pressure agent(s)/conditions, and
  - optionally a second marker sequence, wherein said second marker sequence, when present, is downstream of said signal sequence, but upstream of said modified polynucleotide,
  - thereby producing modified polynucleotide-containing constructs,
- transforming suitable host cells with the modified polynucleotide-containing constructs, and selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., modulated conformational selectivity and/or activation pathway selectivity relative to wild type.

In accordance with a further embodiment of the present invention, there are provided methods to modulate the conformational selectivity and/or activation pathway selectivity of a membrane-spanning protein, said method comprising:
transforming suitable host cells with a construct comprising:
a modified polynucleotide,
a signal sequence, and
one or more marker sequence(s),
wherein:
said marker sequence(s) is/are in-frame with said modified polynucleotide, and encodes one or more genes that overcome the sensitivity of said host to the presence of selective pressure agent(s)/conditions,
said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to modulate the conformational selectivity and/or activation pathway selectivity thereof, and optionally thereafter generating a second library from said first library, said second library comprising a polynucleotide encoding said membrane-spanning protein randomly modified in a sufficient number of amino acid residues so as to modulate the conformational selectivity and/or activation pathway selectivity thereof, and
selecting those cells which survive exposure to said selective pressure agent(s)/conditions (e.g., antibiotic) and identifying the modified polynucleotide-containing construct(s) contained therein.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., modulated conformational selectivity and/or activation pathway selectivity relative to wild type.

In accordance with yet another embodiment of the present invention, there are provided methods to modulate the conformational selectivity and/or activation pathway selectivity of a membrane-spanning protein, said methods comprising selecting those cells which survive exposure to selective pressure agent(s) (e.g., antibiotic) and/or selective pressure conditions, and thereafter identifying the modified polynucleotide-containing construct(s) contained therein, wherein said cells are transformed with:
a modified polynucleotide,
a signal sequence, and
one or more marker sequence(s),
wherein:
said marker sequence is in-frame with said modified polynucleotide, and encodes one or more genes that overcome the sensitivity of said host to the presence of selective pressure agent(s)/conditions,
said modified polynucleotide is obtained by generating a first polynucleotide library wherein a sufficient number of bases of a polynucleotide encoding said membrane-spanning protein and/or a sufficient number of amino acid residues of said membrane-spanning protein are randomly modified so as to modulate the conformational selectivity and/or activation pathway selectivity thereof, and optionally thereafter generating a second library from said first library, said second library comprising a polynucleotide encoding said membrane-spanning protein randomly modified in a sufficient number of amino acid residues so as to modulate the conformational selectivity and/or activation pathway selectivity thereof.

In accordance with yet another embodiment of the present invention, there are provided modified membrane-spanning proteins identified by the above-described methods. Typically, said modified membrane-spanning protein have one or more improved functional properties relative to the wild type membrane-spanning protein, e.g., modulated conformational selectivity and/or activation pathway selectivity relative to wild type.

In accordance with still another embodiment of the present invention, there are provided methods of generating diagnostic and/or therapeutic antibodies, said methods comprising generating an antibody against any of the modified membrane-spanning proteins described herein. Antibody generation can be carried out using techniques that are well known in the art. Antibody selection can be greatly improved by using thermostabilized mutants prepared employing invention methods. See, for example, Hutchings C J et al. 2014 Mabs, 6(1):246-61).

In accordance with yet another embodiment of the present invention, there are provided methods of treating a disease or condition mediated by a membrane-spanning protein, said method comprising administering an effective amount of a therapeutic antibody prepared as described herein to a subject in need thereof.

In accordance with yet another embodiment of the present invention, there are provided methods of treating a disease or condition mediated by a membrane-spanning protein, said method comprising administering an effective amount of a modified membrane-spanning protein as described herein to a subject in need thereof.

In accordance with yet another embodiment of the present invention, there are provided methods of treating a disease or condition mediated by a membrane-spanning protein, said method comprising administering polynucleotide encoding a membrane-spanning protein according to any of the modified membrane-spanning proteins described herein.

The following examples are provided to further illustrate aspects of the invention. These examples are non-limiting and should not be construed as limiting any aspect of the invention.

EXAMPLE 1

Library Generation Phase

Random mutagenesis, optionally coupled with DNA shuffling, can leverage a full range of combinatorial amino acid replacements in multiple positions simultaneously.

Thus, error prone PCR is used to generate a library (first level library) of genes where 8 amino acid residues are randomly mutated after translation per each 1 Kb of DNA (fairly homogeneous frequency of mutation). Optionally, DNA shuffling (StEP, Staggered Extention PCR) may subsequently be used to generate a second library (second level) with genes randomly mutated in about 3 to 15 different amino acids per gene. Roughly 1 ng of this library will contain 1 billion genes; given the amplification method used, about 0.15 billion genes are contained in each ng of DNA used for transformation. Depending on transformation efficiency and effort, about 1 million different genes could be screened each day.

EXAMPLE 2

Construct Design

Figure 2:
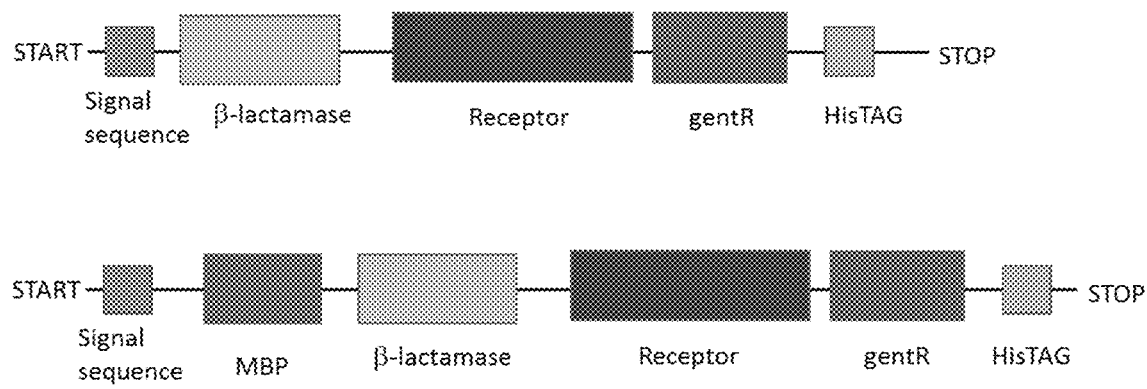
FIG. 2 presents a schematic diagram of two exemplary constructs prepared as described in Example 2, for the expression of membrane proteins in a bacterial selection host, in their wild type or enhanced mutated form. START and STOP refer to translation initiation and termination; boxes indicate genes which translate into functionally independent proteins.

The mutated genes are inserted in a pre-formed construct (plasmid form) containing:
  a signal sequence,
  maltose binding protein (MBP) or beta-lactamase on the receptor's N-terminal side, and
  a kanamycin or gentamicin resistance gene on its C-terminal side.
These domains are all separated by various small oligopeptide linkers. Two exemplary constructs prepared as described herein are illustrated in FIG. 2.

The construct is permanently transcribed in E. coli using constitutive promoters (e.g. Plac) or inducible promoters (e.g. araBAD, T7) with the addition of chemical inducers (e.g. arabinose, IPTG).

EXAMPLE 3

Selection Phase

The construct library containing modified genes is then used to transform E. coli strains (e.g. BL21 or DH10beta). Growth is tested on LB medium with varying concentrations of kanamycin (MIC for untransformed cells is approximately 10 mg/L), both in liquid and agar plates.

An N-terminal truncation (aa 43-424) of the wild type Neurotensin receptor 1 from rat (NTSR1, UniProt P20789) is used as a control system.

About 25 constructs were generated with wild type NTSR1 consisting of combinations of:
  3 different signal sequences (gIIIss, DsbAss, MBPss),
  2 fusion partners (TrxA, MBP),
  several oligopeptide linkers, and
  antibiotic resistance enzymes (NPTII for kanamycin resistance, AAC(3)-1 for gentamicin resistance, TEM-1 β-lactamase for carbenicillin resistance).

Apparent MIC for both antibiotics tested (carbenicillin and gentamicin) increased considerably when E. coli expressed certain constructs containing NTSR1 (>50 mg/L kanamycin, >75 mg/L carbenicillin).

MIC for both antibiotics tested (carbenicillin and kanamycin) also increased when E. coli contained a plasmid encoding the wild type membrane-spanning protein receptor GPR55 from human (UniProt Q9Y2T6) (approximately 25 mg/L kanamycin, 40 mg/L carbenicillin).

EXAMPLE 4

Results

Libraries of mutated GPR55 genes were created containing between about 3 and 15 random mutations (residue) per gene. Selection of plasmids containing enhanced receptor mutants was performed at 50 mg/L kanamycin.

Transformation of E. coli strains with these libraries resulted in the isolation of mutated GPR55 clones that could confer resistance to high concentrations of kanamycin (>50 mg/L) or carbenicillin (>80 mg/L).

Figure 3:
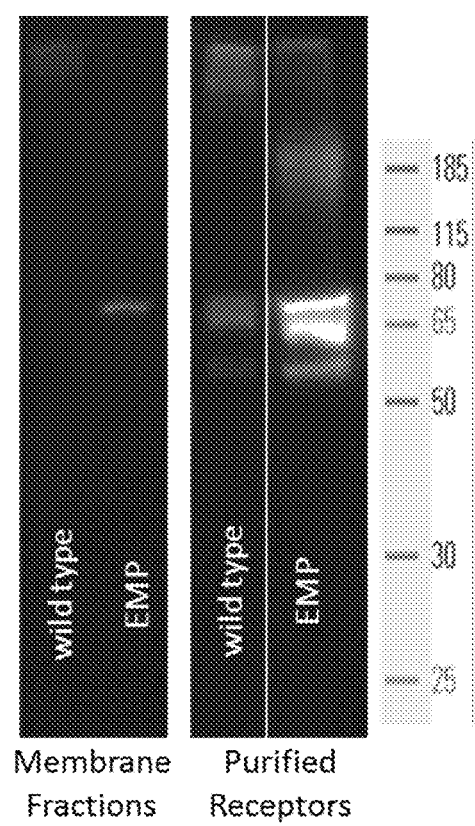
FIG. 3 presents a Western blot of a wild type receptor and its enhanced mutant (also referred to herein as "Enabled Membrane Protein" or "EMP"). Staining of the FLAG-tagged fusion EMP was carried out using an anti-FLAG HRP-conjugated antibody. The protein marker indicates molecular weights in KDa.

Mutated clones are transferred to mammalian expression hosts, including HEK293T by transfection using the pcDNA3.1 vector. Expression is observed to increase by >5-fold over constructs containing wild type GPR55, as judged by electrophoretic (see, for example, FIG. 3) and fSEC techniques.

Figure 4:
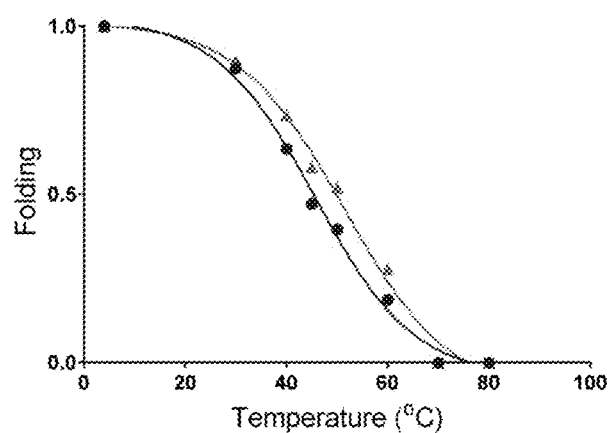
FIG. 4 presents thermal unfolding curves measured using fluorescent size exclusion chromatography (fSEC) on purified receptors in a protein-detergent complex after one round of mutagenesis. The wild type receptor is shown in closed circles, whereas a stabilized mutant is shown in triangles.

Mutated clones are expressed and purified; the resulting protein-detergent complex samples demonstrate an increase in thermostability of up to 7° C. over wild type after one round of mutagenesis (as judged by fSEC (see, for example, FIG. 4) and fluorimetric techniques).

Figure 5:
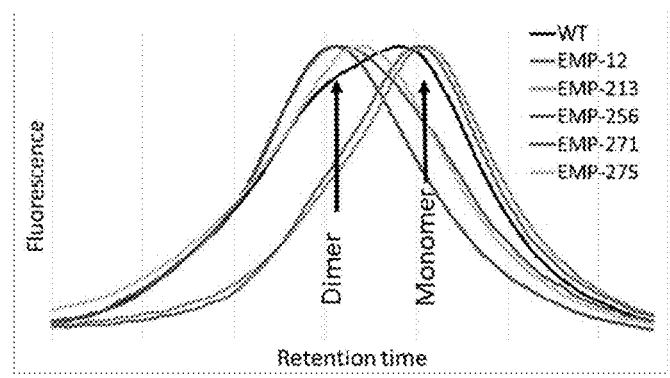
FIG. 5 presents normalized fSEC peaks of purified wild type (black trace) and mutant receptors (EMPs). The peaks corresponding to monomer and dimer of the analyzed GPCR (estimated oligomeric state of the analyzed samples) are indicated with a black arrow.

Mutated clones also demonstrate a more homogeneous oligomeric state compared to wild type when receptor samples are purified in ligand free form (see, for example, FIG. 5).

When using hyperthermophilic species (e.g. *Thermus thermophilus*) as a selection host, the protein melting temperature (in the thermal unfolding format) of the identified mutants is expected to be superior when compared to a selection process performed in E. coli. (i.e., more than 10° C. higher than wild type).

EXAMPLE 5

Antibody selection is expected to greatly improve (become easier) when using said thermostabilized mutants as selecting antigen in phage or yeast display (or similar antibody screening, as well as antibody generation). Generating antibody should also be facilitated when these thermostabilized mutants are used as immunogen in-vivo in protein form, or using sequence encoding DNA or RNA in an appropriate animal or human host, or in association with an appropriate immunization vehicle or appropriate immune formulation used as an adjuvant or delivery vehicle (see, for example, Hutchings C J et al. 2014 Mabs, 6(1):246-61).

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. A method of modulating one or more functional properties of a membrane-spanning protein, said method comprising:
   (a) generating a first polynucleotide library from a starting polynucleotide that encodes the membrane-spanning protein, wherein a sufficient number of bases of said starting polynucleotide are randomly modified so as to modulate the one or more functional properties of the membrane-spanning protein,
   (b) generating a second polynucleotide library from said first polynucleotide library by DNA shuffling, said second polynucleotide library comprising a modified polynucleotide encoding a modified membrane-spanning protein comprising said one or more modulated functional properties,
   (c) inserting the modified polynucleotides of said second polynucleotide library into a construct comprising:
   a signal sequence,
   a first marker sequence, wherein said first marker sequence is in-frame with said modified polynucleotide, is downstream of said modified polynucleotide, and encodes a polypeptide that overcomes the sensitivity of a host cell to the presence of a first selective pressure agent or condition and the polypeptide is fused to said modified membrane-spanning protein, and
   a second marker sequence, wherein said second marker sequence is in-frame and downstream of said signal sequence, but upstream of said modified polynucleotide, is different from the first marker sequence and encodes a polypeptide that overcomes the sensitivity of a host cell to the presence of a second selective pressure agent or condition, and is fused to said modified membrane-spanning protein, thereby producing modified polynucleotide-containing constructs,
   (d) transforming a plurality of host cells with the modified polynucleotide-containing constructs to obtain a plurality of transformed host cells;
   (e) culturing the transformed host cells in the presence of said first and second selective pressure agents/conditions, wherein the concentration/condition levels of said first and second selective pressure agents/conditions are higher than the concentration/condition levels of said first and second selective pressure agents/conditions used for culturing an equivalent host cell transformed with the starting polynucleotide;
   (f) selecting a host cell from step (e) that survives exposure to said first and second selective pressure agents/conditions; and
   (g) identifying the modified polynucleotide-containing construct(s) contained therein;
   wherein the surviving host cells from step (f) express the modified membrane-spanning protein having the one or more modulated functional properties relative to the membrane-spanning protein encoded by the starting polynucleotide.

2. The method of claim 1 wherein said one or more modulated functional properties are selected from the group consisting of an increased level of expression of said modified membrane-spanning protein, an increased stability of said modified membrane-spanning protein, an increased homogeneity of said modified membrane-spanning protein, an increased crystallizability of said modified membrane-spanning protein, an increased antigenicity of said modified membrane-spanning protein, an increased immunogenicity of said modified membrane-spanning protein, a modulated conformational selectivity and/or activation pathway selectivity of said modified membrane-spanning protein.

3. The method of claim 2, wherein said one or more modulated functional properties comprise an increased level of expression of said modified membrane spanning protein, wherein said increase is at least 5 fold.

4. The method of claim 2, wherein said one or more modulated functional properties comprise an increased stability of said modified membrane spanning protein, wherein said stability is an increase in thermostability.

5. The method of claim 4, wherein said increase in thermostability is stability at an increase of at least 7° C.

6. The method of claim 1 wherein said membrane-spanning protein is a G-protein coupled receptor (GPCR).

7. The method of claim 1, wherein said GPCR is a GPR55 or a Neurotensin receptor 1 (NTSR1).

8. The method of claim 1, wherein said first selective pressure agent is a first antibiotic.

9. The method of claim 1, wherein said second selective pressure agent is a second antibiotic.

10. The method of claim 1, wherein said modified membrane- spanning protein comprises at least 3, 4, 5, 6, 7, 8, 9, 10, 11, 12, 13, 14, or 15 modified amino acid residues relative to the membrane-spanning protein.

11. The method of claim 1, further comprising isolating the modified polynucleotide containing constructs.

12. The method of claim 7, further comprising verifying the occurrence of said one or more modulated functional properties by:
   inserting the modified polynucleotide containing constructs into a suitable host cell, expressing said modified polynucleotide, and characterizing the modified membrane-spanning protein encoded by the modified polynucleotide.

13. The method of claim 12, further comprising isolating the modified membrane-spanning protein.

14. The method of claim 1, further comprising:
randomly reverting said modified residues back,
re-selecting in the presence of selective pressure agent(s)/conditions(s), and
re-characterizing the modulated functional properties in order to identify a minimum working set of mutations.

15. The method of claim 1 wherein the host cell is selected from the group consisting of a bacterial cell, a yeast cell, an insect cell and a mammalian cell.

16. The method of claim 1, wherein the first marker sequence encodes a thioredoxin 1 or a beta-lactamase.

17. The method of claim 1, wherein the second marker sequence is a kanamycin resistance gene or a gentamicin resistance gene.

* * * * *